United States Patent
Okamoto et al.

(10) Patent No.: US 10,429,338 B2
(45) Date of Patent: Oct. 1, 2019

(54) GAS SENSOR AND GAS CONCENTRATION MEASURING METHOD USING THE SAME

(71) Applicant: NGK INSULATORS, LTD., Nagoya-shi, Aichi (JP)

(72) Inventors: Taku Okamoto, Nagoya (JP); Noriko Hirata, Nagoya (JP); Yuki Nakayama, Nagoya (JP); Kosuke Monna, Aichi (JP)

(73) Assignee: NGK Insulators, Ltd., Nagoya (JP)

( * ) Notice: Subject to any disclaimer, the term of this patent is extended or adjusted under 35 U.S.C. 154(b) by 75 days.

(21) Appl. No.: 15/686,239

(22) Filed: Aug. 25, 2017

(65) Prior Publication Data

US 2018/0059046 A1 Mar. 1, 2018

(30) Foreign Application Priority Data

Aug. 26, 2016 (JP) .................. 2016-165735

(51) Int. Cl.
*G01N 27/407* (2006.01)
*G01N 27/403* (2006.01)
*G01N 27/406* (2006.01)

(52) U.S. Cl.
CPC ..... *G01N 27/4077* (2013.01); *G01N 27/4067* (2013.01); *G01N 27/4074* (2013.01); *G01N 27/4076* (2013.01)

(58) Field of Classification Search
CPC .......... G01N 27/4077; G01N 27/4067; G01N 27/407; G01N 27/4071; G01N 27/4074; G01N 27/403
See application file for complete search history.

(56) References Cited

U.S. PATENT DOCUMENTS

| 6,632,338 B2 | 10/2003 | Fujii et al. |
| 2010/0282619 A1* | 11/2010 | Wang ................ G01N 27/4074 205/780.5 |
| 2013/0248363 A1* | 9/2013 | Sugaya ............. G01N 27/4075 204/429 |

FOREIGN PATENT DOCUMENTS

| JP | 2002-071632 A | 3/2002 |
| JP | 2006-038496 A | 2/2006 |
| JP | 2012-173147 A | 9/2012 |

* cited by examiner

*Primary Examiner* — Susan D Leong
(74) *Attorney, Agent, or Firm* — Mattingly & Malur, PC

(57) ABSTRACT

A gas sensor in which an electrode is prevented from being poisoned is provided. A mixed-potential type gas sensor includes a sensor element composed a solid electrolyte. The sensor element includes: a measurement gas introduction space having an open end at a distal end and extending in a longitudinal direction; a sensing electrode provided on an inner side of the measurement gas introduction space; and a heater configured to heat the sensor element. The concentration of the gas component is determined based on a potential difference between the sensing electrode and a reference electrode, while the heater heats the sensor element so that a place having a temperature higher than the temperature of the sensing electrode and the melting point of a poisoning substance exists between the open end and the sensing electrode and the temperature decreases toward the sensing electrode.

4 Claims, 12 Drawing Sheets

F I G. 1
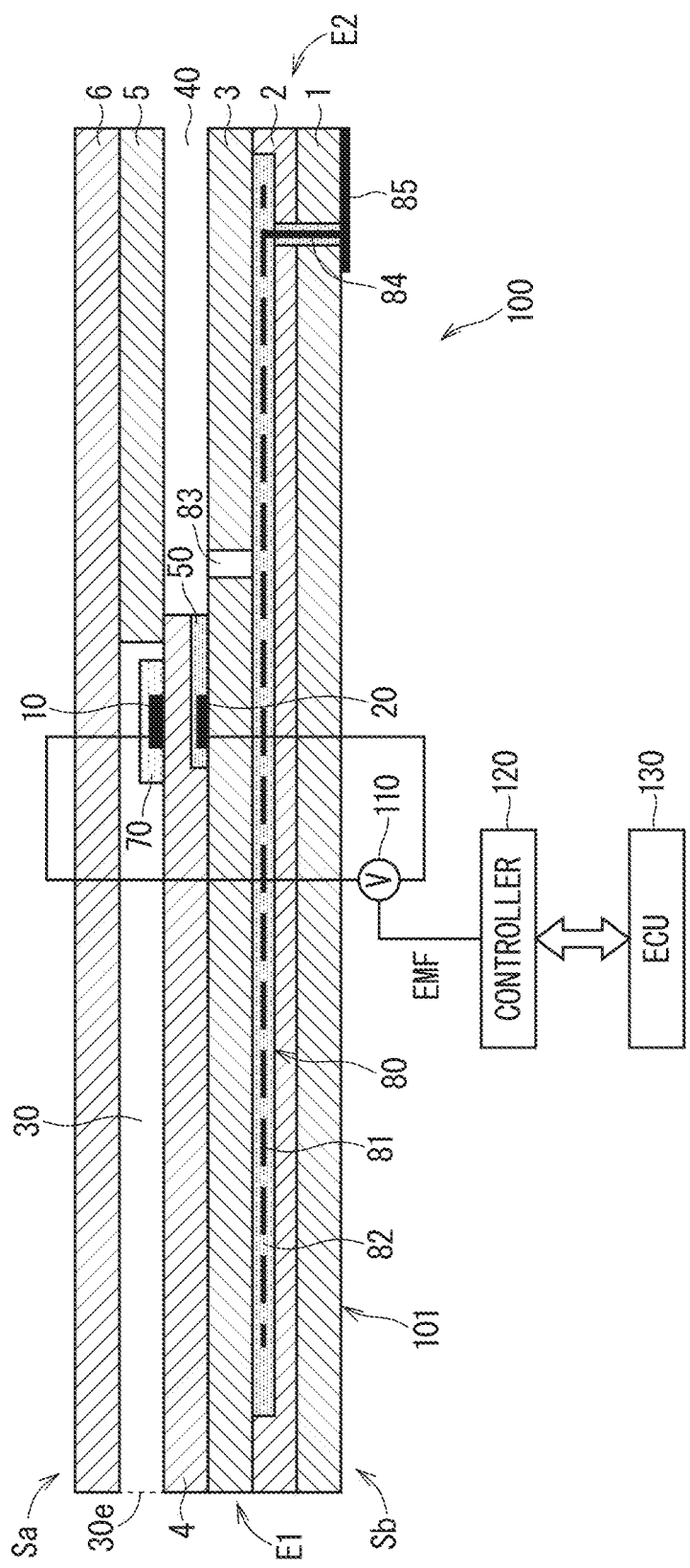

F I G. 2
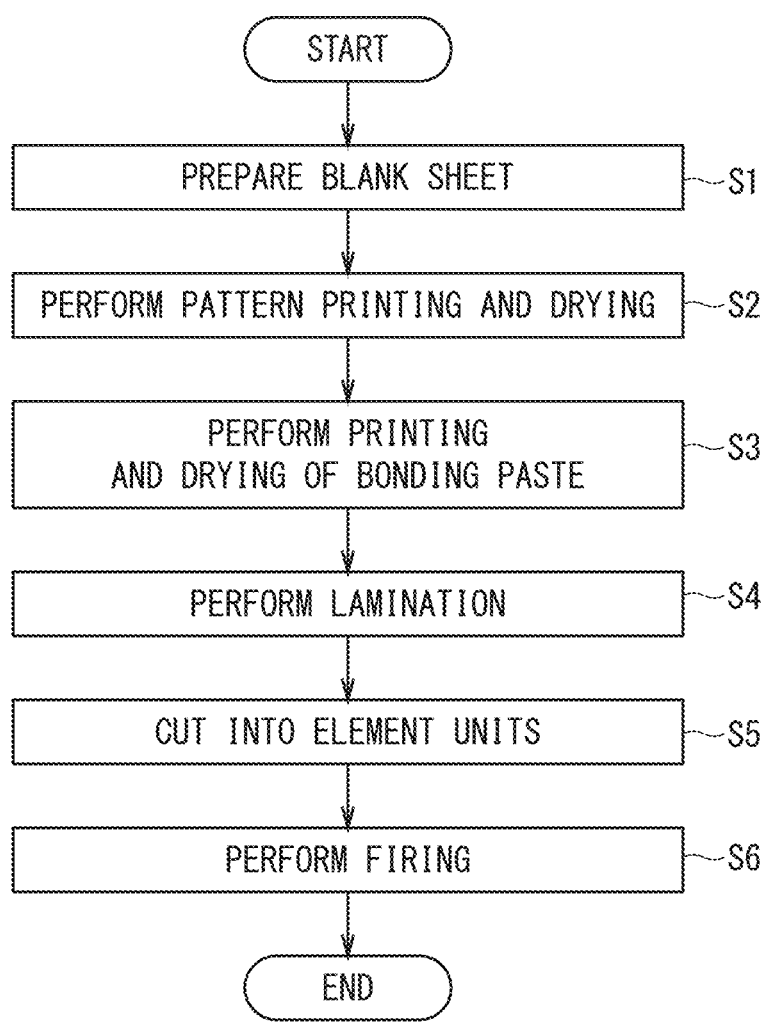

F I G. 11
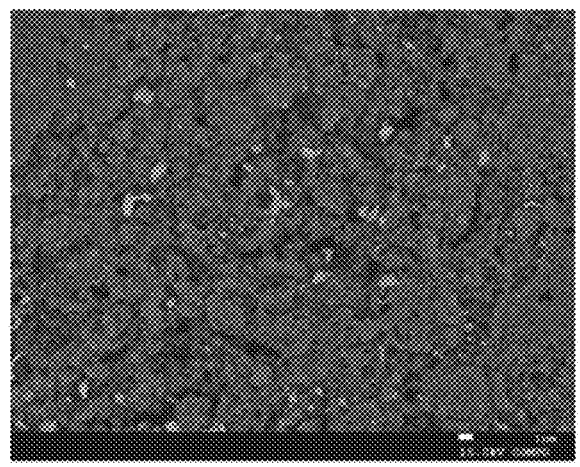

GAS SENSOR AND GAS CONCENTRATION MEASURING METHOD USING THE SAME

BACKGROUND OF THE INVENTION

Field of the Invention

The present invention relates to a gas sensor configured to detect a predetermined gas component of a measurement gas, and particularly relates to prevention of poisoning of a sensing electrode thereof.

Description of the Background Art

Measurement of the concentration of a predetermined target gas component such as a hydrocarbon gas or ammonia included in an exhaust gas has been increasingly required because of recent reinforcement of exhaust gas regulation. In some gas sensors used for such gas concentration measurement, a protective layer is provided on the surface of a sensor element mainly formed of a solid electrolyte.

The protective layer provided to the sensor element have functions of (1) trapping of a poisoning substance containing, for example, phosphorus (P), (2) prevention of evaporation of a material (in particular, a noble metal such as Pt or Au) of an electrode provided on the surface of an element, and (3) a molecular sieve that allows only a measurement gas to reach at a three-phase interface. Some publicly known gas sensors have a configuration in which a plurality of layers that share the functions (1) to (3) respectively, are provided on the surface of the sensor element (for example, refer to Japanese Patent Application Laid-Open No. 2002-71632, Japanese Patent Application Laid-Open No. 2012-173147, and Japanese Patent Application Laid-Open No. 2006-38496).

The above-described functions (1) to (3) need to be achieved for a gas sensor to desirably operate, and thus it is inappropriate to remove the protective layer from the sensor element.

In the gas sensor disclosed in Japanese Patent Application Laid-Open No. 2012-173147, the porosity and pore size of a porous protective layer formed on an electrode protective layer to function as a trapping layer are optimized to achieve reliable trapping of a poisoning substance and prevention of clogging of the protective layer are achieved. However, in some cases, it is difficult to sufficiently obtain these effects depending on an environment in which the gas sensor is used and operation conditions (for example, a travel distance and a use place). Moreover, any poisoning substance adhering to the porous protective layer potentially reaches at an electrode through diffusion thereafter, causing electrode poisoning. In other words, a risk of clogging or the like attributable to change in a discharge condition and characteristics of the poisoning substance, which is caused by change in the use environment and the operation conditions, may still remain, even though the technology disclosed in Japanese Patent Application Laid-Open No. 2012-173147 is adopted.

When a gas sensor employing a scheme that a poisoning substance is trapped by a protective layer is used under an environment with a small amount of the poisoning substance, clogging may not occur but a small amount of the poisoning substance adheres to the surfaces of particles in the protective layer. Thus, when the gas sensor is continuously used in this state, the poisoning substance adhering to the protective layer moves toward an electrode nearby through surface diffusion, collaterally causing poisoning of the electrode in some cases. In other words, when the protective layer traps a poisoning component, the electrode poisoning may still occur as a result of the material movement in some cases since the protective layer is disposed near the electrode.

This indicates that trapping of the poisoning substance by the protective layer near the electrode itself contains the risk of electrode poisoning.

SUMMARY OF THE INVENTION

The present invention relates to a gas sensor configured to detect a predetermined gas component of a measurement gas, and is particularly directed to prevention of poisoning of a sensing electrode thereof.

According to the present invention, a mixed-potential type gas sensor for sensing a predetermined gas component in a measurement gas includes a sensor element composed of an oxygen-ion conductive solid electrolyte. The sensor element includes: a measurement gas introduction space having an open end at a distal end of the sensor element and extending in an element longitudinal direction; a sensing electrode formed of a cermet of a noble metal and an oxygen-ion conductive solid electrolyte and provided on a side opposite to the open end in the measurement gas introduction space; a reference electrode formed of a cermet of Pt and an oxygen-ion conductive solid electrolyte; and a heater configured to heat the sensor element. The gas sensor is configured to determine the concentration of the predetermined gas component based on a potential difference between the sensing electrode and the reference electrode. When the gas sensor calculates the concentration of the predetermined gas component, the heater heats the sensor element so that a high temperature place having a temperature higher than the temperature of the sensing electrode and the melting point of a poisoning substance which is determined or estimated in advance exists between the open end and the sensing electrode and so that the temperature decreases toward the sensing electrode between the high temperature place and the sensing electrode in a direction toward the sensing electrode from the open end.

According to the present invention, in a method of measuring the concentration of a predetermined gas component in a measurement gas through a mixed-potential type gas sensor, the gas sensor includes a sensor element composed of an oxygen-ion conductive solid electrolyte. The sensor element includes: a measurement gas introduction space having an open end at a distal end of the sensor element and extending in an element longitudinal direction; a sensing electrode formed of a cermet of a noble metal and an oxygen-ion conductive solid electrolyte and provided on a side opposite to the open end in the measurement gas introduction space, a reference electrode formed of a cermet of Pt and an oxygen-ion conductive solid electrolyte; and a heater configured to heat the sensor element. The method includes the processes of: a) contacting the distal end of the sensor element with the measurement gas and contacting the reference electrode with a reference gas; b) heating, in a contact state achieved through the process a), the sensor element by the heater, so that a high temperature place having a temperature higher than the temperature of the sensing electrode and the melting point of a poisoning substance which is determined or estimated in advance exists between the open end and the sensing electrode so that and the temperature decreases toward the sensing electrode between the high temperature place and the sensing electrode in a direction toward the sensing electrode from the open end; and c) determining the concentration of the predetermined gas component based on a potential difference between the sensing electrode and the reference electrode while the sensor element is heated through the process b).

According to these inventions described above, when the concentration of a measurement target gas component is determined by the gas sensor, a poisoning substance entering into the measurement gas introduction space through the open end is trapped before reaching at a position at which the sensing electrode is disposed. Therefore, the sensing electrode is desirably prevented from being poisoned. With this configuration, no degradation of a sensitivity characteristic due to the poisoning substance occurs when the gas sensor is continuously used.

Thus, the present invention is intended to provide a gas sensor in which an electrode in a sensor element is desirably prevented from being poisoned.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a diagram illustrating a gas sensor 100;

FIG. 2 is a flowchart illustrating the process of manufacturing a sensor element 101;

FIG. 11 is a surface SEM image of the electrode protective layer 70 of the gas sensor 100, the sensitivity characteristic of which is evaluated after a poisoning test.

DESCRIPTION OF THE PREFERRED EMBODIMENTS

<Configuration of Gas Sensor>

Figure 3:
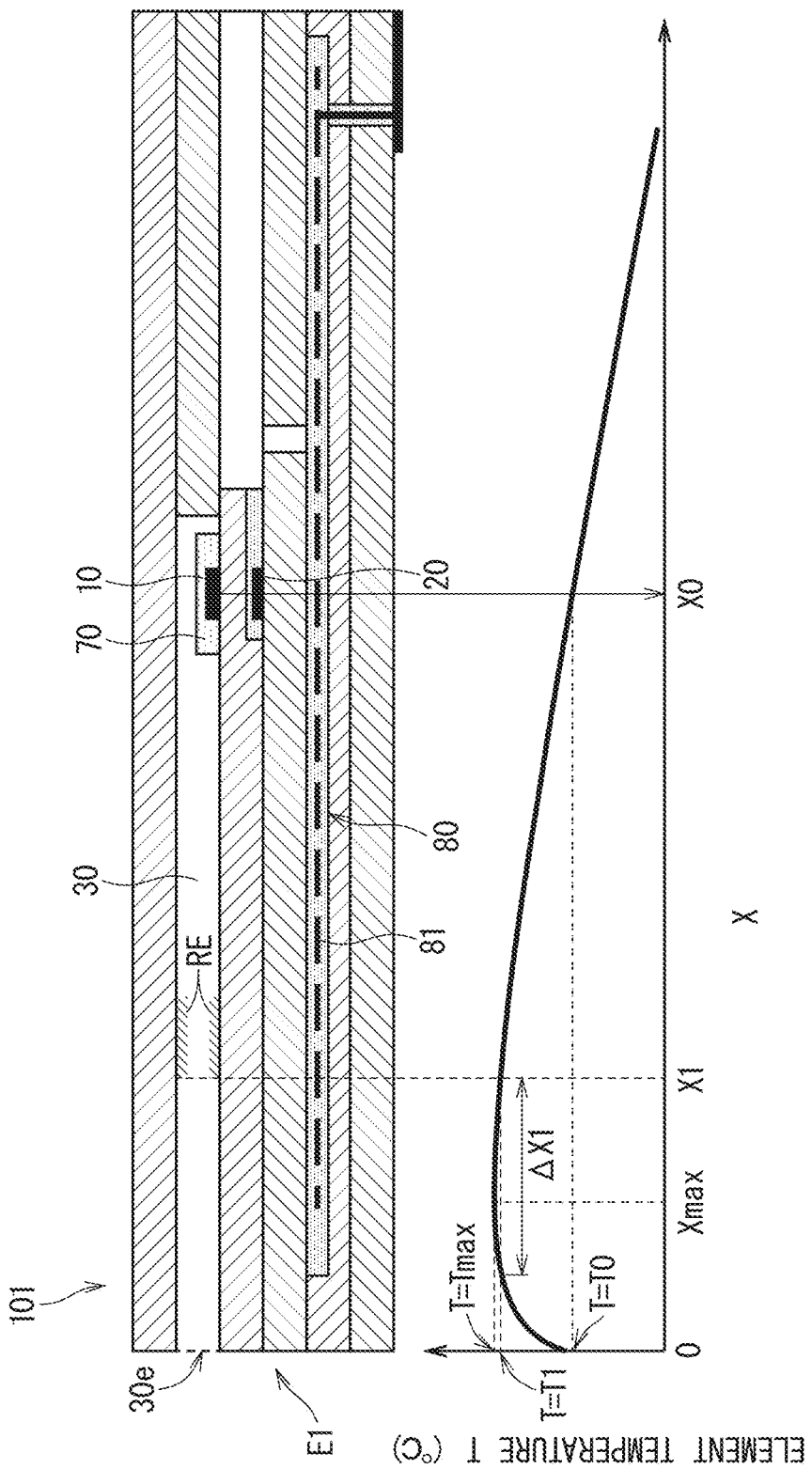
FIG. 3 is a diagram illustrating a Temperature Profile of the sensor element 101.

FIG. 1 is a diagram illustrating a gas sensor 100 as an exemplary gas sensor according to a preferred embodiment of the present invention.

The gas sensor 100 mainly includes a sensor element 101, and a controller 120 configured to control operation of the gas sensor 100 including the sensor element 101.

The gas sensor 100 is what is called a mixed-potential type gas sensor. Schematically, the gas sensor 100 determines the concentration of a target gas component of a measurement gas by using a potential difference between a sensing electrode 10 and a reference electrode 20, which are provided inside the sensor element 101 mainly formed of ceramics such as zirconia ($ZrO_2$) as an oxygen-ion conductive solid electrolyte. The potential difference is caused by a difference between the concentrations of the measurement target gas near the respective electrodes based on the principle of mixed potential.

More specifically, the gas sensor 100 preferably determines the concentration of a predetermined gas component (detection gas component) of a measurement gas that is an exhaust gas existing in an exhaust pipe of an internal-combustion engine such as a diesel engine or a gasoline engine. When the detection gas component is an unburned hydrocarbon gas in the exhaust gas, the unburned hydrocarbon gas includes carbon monoxide (CO) in addition to typical hydrocarbon gasses of, for example, $C_2H_4$, $C_3H_6$, and n-C8 (categorized as hydrocarbon by chemical formulae). The measurement target may be other kinds of gasses including ammonia. In such a case, the gas sensor 100 is controlled by the controller 120 based on a control instruction from an electronic control device (ECU) 130 configured to control the entire internal-combustion engine.

The sensor element 101 illustrated in FIG. 1 has a long plate or bar shape. The sensor element 101 mainly includes a measurement gas introduction space 30, a reference gas introduction space 40, and a reference gas introduction layer 50 in addition to the sensing electrode 10 and the reference electrode 20 described above.

The sensor element 101 has a structure in which six layers of a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each made of an oxygen-ion conductive solid electrolyte, are laminated in this order from the bottom side of in FIG. 1. The sensor element 101 additionally includes other components mainly between the layers or on the outer peripheral surface of the element. The solid electrolyte forming the six layers has fine air-tightness. The sensor element 101 is manufactured by, for example, laminating ceramics green sheets corresponding to individual layers, which have been subjected to a predetermined process and printing of electrodes and circuit patterns, and then, by integrating the laminated layers through firing.

However, it is not an essential aspect for the gas sensor 100 to include the sensor element 101 as such a six-layer laminated body. The sensor element 101 may be a laminated body of a larger or smaller number of layers or may have no laminated structure.

In the following description, for sake of convenience, the surface located as the upper surface of the sixth solid electrolyte layer 6 in FIG. 1 is referred to as a front surface Sa of the sensor element 101, and the surface located as the lower surface of the first solid electrolyte layer 1 is referred to as a back surface Sb of the sensor element 101. In the determination of the concentration of the detection gas component in the measurement gas with the gas sensor 100, a predetermined range starting from a distal end E1 being one end of the sensor element 101, which includes at least the sensing electrode 10, is disposed in an atmosphere of the measurement gas, whereas the other portion including a base end E2 opposite to the distal end E1 is disposed so as not to contact with the atmosphere of the measurement gas.

The sensing electrode 10 is an electrode for sensing the measurement gas. The sensing electrode 10 is formed as a porous cermet electrode of a Pt containing a predetermined fraction of Au, namely Pt—Au alloy and zirconia. The sensing electrode 10 is provided in a substantially rectangular shape in plan view in the measurement gas introduction space 30.

The measurement gas introduction space 30 is an internal space provided on a side of the distal end E1 of the sensor element 101 and extending from an open end 30e in an element longitudinal direction. The measurement gas containing the measurement target gas component is introduced into the measurement gas introduction space 30 through the exhaust pipe, in the state that the gas sensor 100 is attached to the exhaust pipe of an internal-combustion engine. The sensing electrode 10 is provided at a most inner part of the measurement gas introduction space 30 from the distal end E1 (in other words, at a position opposite to the open end 30e in the element longitudinal direction).

In the case exemplarily illustrated in FIG. 1, the measurement gas introduction space 30 is provided in such a manner that a space communicated with the exterior is provided in a part of the fifth solid electrolyte layer 5 on the distal end E1 of the sensor element 101. More specifically, upper end and lower end of the measurement gas introduction space 30 in FIG. 1 are partitioned by the fourth solid electrolyte layer 4 and the sixth solid electrolyte layer 6, respectively, and a side end is partitioned by the fifth solid electrolyte layer 5.

The length of the measurement gas introduction space 30 in the element longitudinal direction may be set as appropriate in accordance with the size of each component of the sensor element 101.

Catalytic activity of the sensing electrode 10 to the detection gas components are disabled according to each predetermined concentration range by preferably determining the composition of the Pt—Au alloy being its constituent material. That is, decomposition reaction of the detection gas component at the sensing electrode 10 is prevented. Accordingly, in the gas sensor 100, the potential of the sensing electrode 10 selectively varies with respect to (has a correlation with) the detection gas component in accordance with its concentration. In other words, the sensing electrode 10 is provided to have high dependence of potential on the concentration for the detection gas components in each predetermined concentration range, while having low dependence of potential on the concentration for other components of the measurement gas.

For example, in the case that the detection gas component is an unburned hydrocarbon gas in an exhaust gas, the sensing electrode 10 is formed to have an Au abundance ratio of 0.3 to 2.5, so that it has significant concentration dependence on potential in a concentration range of 0 ppmC to 4000 ppmC approximately of the unburned hydrocarbon gas.

In the present specification, the Au abundance ratio is an area ratio of a portion covered with Au to a portion at which Pt is exposed in the surface of the noble metal particles forming the sensing electrode 10. In the present specification, the Au abundance ratio is calculated using a relative sensitivity coefficient method from peak intensities of peaks detected for Au and Pt obtained by X-ray photoelectron spectroscopy (XPS). The Au abundance ratio is one when the area of the portion at which Pt is exposed is equal to the area of the portion covered with Au.

A conductive paste used to form the sensing electrode 10 by printing can be produced by using an Au ion-containing liquid as an Au starting material and mixing the Au ion-containing liquid with powdered Pt, powdered zirconia, and a binder. Any binder, which can disperse any other raw material to the printable extent and vanishes through firing, may be appropriately selected.

The Au ion-containing liquid is obtained by dissolving a salt containing an Au ion or an organometallic complex containing an Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the sensing electrodes 10 formed in the sensor element 101 obtained through the above-mentioned manufacturing process contain Au mainly as an elemental substrate or an alloy with Pt.

Alternatively, a conductive paste for a sensing electrode may be prepared by using coated powder, which is obtained by coating powdered Pt with Au, as a starting raw material, instead of preparing the paste through liquid-state Au mixing as described above. In such a case, a conductive paste for a sensing electrode is prepared by mixing the coated powder, zirconia powder, and a binder. Here, the coated powder may be obtained by covering the particle surface of powdered Pt with an Au film or applying Au particles to Pt powder particles.

The reference electrode 20 is an electrode having a substantially rectangular shape in plan view, which is provided inside the sensor element 101 and serves as a reference in the determination of the concentration of the measurement gas. The reference electrode 20 is provided as a porous cermet electrode of Pt and zirconia.

More specifically, the reference electrode 20 is provided in the reference gas introduction layer 50 communicated with the reference gas introduction space 40 and below the sensing electrode 10 in plan view from the surface Sa in a thickness direction (direction in which the solid electrolyte layers are laminated) of the sensor element 101.

The reference electrode 20 may be formed so as to have a porosity of 10% or more and 30% or less and a thickness of 5 μm or larger and 15 μm or smaller. The reference electrode 20 may have a plane size equivalent to or smaller than that of the sensing electrode 10.

The reference gas introduction space 40 is an internal space provided near the base end E2 of the sensor element 101. Air (oxygen), serving as a reference gas in the determination of the concentration of the detection gas component is externally introduced into the reference gas introduction space 40.

In the case exemplarily illustrated in FIG. 1, the reference gas introduction space 40 is provided in such a manner that a space communicated with the exterior is provided in a part of the fourth solid electrolyte layer 4 on the base end E2 of the sensor element 101. More specifically, upper end and lower end of the reference gas introduction space 40 in FIG. 1 are partitioned by the third solid electrolyte layer 3 and the fifth solid electrolyte layer 5, respectively, and a side end is partitioned by the fourth solid electrolyte layer 4.

The reference gas introduction layer 50 is an alumina porous layer communicated with the reference gas introduction space 40. In the case exemplarily illustrated in FIG. 1, the reference gas introduction layer 50 is provided between the third solid electrolyte layer 3 and the fourth solid electrolyte layer 4.

When the gas sensor 100 is used, the surrounding of the reference electrode 20 provided in the reference gas introduction layer 50 is always filled with air (oxygen) introduced through the reference gas introduction space 40 and the reference gas introduction layer 50. With this configuration, the reference electrode 20 always has a constant potential when the gas sensor 100 is used.

The reference gas introduction space 40 and the reference gas introduction layer 50 are provided so as not to come into contact with a measurement gas owing to their surrounding solid electrolytes. This prevents the reference electrode 20 from coming into contact with the measurement gas even when the sensing electrode 10 is exposed to the measurement gas.

Although the reference electrode 20 has a constant potential, the potential of the sensing electrode 10 depends on the concentration of the detection gas component as described above. Thus, a potential difference in accordance with the concentration of the detection gas component is occurred between the sensing electrode 10 and the reference electrode 20. This potential difference is measured by a potentiometer 110 provided to the gas sensor 100.

Wires between the potentiometer 110 and each of the sensing electrode 10 and the reference electrode 20 are simplified in the drawings. However, in the actual sensor element 101, a connection terminal (not illustrated) for each electrode is provided on the surface Sa or the back surface Sb closer to the base end E2, and a wiring pattern (not illustrated) connecting each electrode and the corresponding connection terminal is formed on the surface Sa and inside the element. The sensing electrode 10 and the reference electrode 20 are each electrically connected with the potentiometer 110 through the wiring pattern and the connection terminal.

Hereinafter, a potential difference between the sensing electrode 10 and the reference electrode 20, which is measured by the potentiometer 110, is also referred to as a sensor output EMF or simply an EMF. The sensing electrode 10, the reference electrode 20, and the solid electrolyte between the electrodes are also referred to as a sensing cell. Thus, the sensing cell is a mixed potential cell.

The sensor element 101 also includes an electrode protective layer 70. The electrode protective layer 70 is an alumina porous layer covering at least the sensing electrode 10 and exposed in the measurement gas introduction space 30. The electrode protective layer 70 not only prevents evaporation of Pt and Au constituting the sensing electrode 10, but also functions as a molecular sieve configured to allow only the measurement gas to reach at a three-phase interface. The electrode protective layer 70 is provided so as to have a configuration (pore size, porosity, and thickness) with which the reach of the measurement gas at the sensing electrode 10 is not virtually controlled.

The electrode protective layer 70 is exposed toward the measurement gas introduction space 30 and is therefore exposed to the measurement gas, but it is not necessarily formed with taken into account clogging due to a poisoning substance. This is because adhesion of a poisoning substance in the measurement gas to the electrode protective layer 70 is desirably prevented from a reason described later. In other words, the gas sensor 100 according to the present preferred embodiment does not need a function to achieve protection from a poisoning substance, and accordingly, requirement on formation thereof is relaxed as compared to a conventional technology in which a protective layer is provided to protect, from a poisoning substance, an electrode provided on the surface of a sensor element.

The sensor element 101 further includes a heater part 80. The heater part 80 mainly includes a heater 81, a heater insulating layer 82, a pressure diffusing hole 83, a through-hole 84, and a heater electrode 85.

The heater 81 is formed so as to be sandwiched between the second solid electrolyte layer 2 and the third solid electrolyte layer 3 above and below. The heater 81 is provided so as to snake in the element longitudinal direction (in a meander shape). The heater 81 is disposed across at least a range extending the vicinity of the distal end E1 to below the sensing cell in the element longitudinal direction.

The heater insulating layer 82 is provided between the heater 81 and each of the second solid electrolyte layer 2 and the third solid electrolyte layer 3 to electrically insulate between the heater 81 and each of the second solid electrolyte layer 2 and the third solid electrolyte layer 3. The heater insulating layer 82 is made of, for example, alumina.

The heater 81 generates heat by being externally supplied with power through the heater electrode 85 provided on the back surface Sb of the sensor element 101 (the lower surface of the first solid electrolyte layer 1 in FIG. 1). The heater electrode 85 and the heater 81 are electrically connected with each other through a heater lead disposed inside the heater insulating layer 82 and inside the through-hole 84 penetrating from the heater insulating layer 82 to the back surface Sb. The power supply to the heater 81 is controlled by the controller 120 based on a control instruction from the ECU 130.

The pressure diffusing hole 83 is a part that penetrates through the third solid electrolyte layer 3 and through which the heater insulating layer 82 and the reference gas introduction space 40 are communicated with each other. The pressure diffusing hole 83 is provided to mitigate an internal pressure rise associated with a temperature rise in the heater insulating layer 82 along with a temperature increase.

In the gas sensor 100, when the concentration of the detection gas component is determined, the heater 81 generates heat so that each component of the sensor element 101 is heated and kept at a temperature suitable for operation. Specifically, the sensing cell is heated to a temperature T0 of 400° C. or higher and 600° C. or lower, preferably 450° C. or higher and 550° C. or lower. A side closer to the distal end E1 than the sensing cell is heated to a temperature higher than that of the sensing cell. In the gas sensor 100, the position of the sensing cell, a range in which the heater 81 extends, a positional relation between the sensing cell and the heater 81, and further, the manner of heating by the heater 81 are set so that such a heating temperature is suitably achieved. However, this specific configuration is not limited to one but has various kinds of variations. Temperature distribution (temperature profile) in the sensor element 101 will be described later.

In the gas sensor 100 having the above-described configuration, while the sensing cell is heated to the predetermined temperature T0 by the heater 81, the potential of the reference electrode 20 being disposed in an atmosphere of air (having a constant oxygen concentration) is maintained constant, but the potential of the sensing electrode 10 has dependency on the concentration of the detection gas component in the measurement gas. Accordingly, a potential difference in accordance with the concentration of the detection gas component is generated between the sensing electrode 10 and the reference electrode 20. This potential difference is output, as the sensor output EMF, to the controller 120 configured to control operation of the gas sensor 100. This output value provided to the controller 120 is further provided to the ECU 130, and the ECU 130 performs arithmetic processing based on the output value, thereafter to obtain the concentration of the detection gas component around the sensor element 101. In other words, the ECU 130 functions as concentration determining means configured to determine the concentration of the detection gas component.

A certain functional relationship (referred to as sensitivity characteristics) holds between the concentration of each of the detection gas components and the sensor output. Thus, a plurality of different mixed gases, each of which has a known concentration of the detection gas component, are prepared as the measurement gases in advance, and the sensor output for each measurement gas is measured, thereby experimentally identifying sensitivity characteristics. Then, these sensitivity characteristics are stored in the ECU 130. When the gas sensor 100 is actually used, the value of the sensor output EMF, which varies momentarily in accordance with the concentration of the detection gas component in a measurement gas, is compared against the sensitivity characteristics at the ECU 130, resulting that the concentration of the detection gas component is obtained. Accordingly, the concentration of the detection gas component in the measurement gas can be determined almost in real time.

<Process of Manufacturing Sensor Element>

Next, the outline of the process of manufacturing the sensor element 101 will be described. Generally speaking, irrespective of difference between specific constitutions thereof, the sensor element 101 is manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

FIG. 2 is a flowchart illustrating the process of manufacturing the sensor element 101. First, blank sheets (not shown) that are green sheets having no pattern formed thereon are prepared (step S1). Specifically, six blank sheets corresponding to the first solid electrolyte layer 1, the second solid electrolyte layer 2, the third solid electrolyte layer 3, the fourth solid electrolyte layer 4, the fifth solid electrolyte layer 5, and the sixth solid electrolyte layer 6 are prepared. A plurality of sheet holes used for positioning in printing and lamination are provided in the blank sheets in advance. Such sheet holes are formed in advance through, for example, punching by a punching device. For a green sheet whose corresponding layer forms the measurement gas introduction space 30, the reference gas introduction space 40, and the reference gas introduction layer 50, a penetrating portion corresponding to these internal spaces is also provided in advance through, for example, punching as described above. Not all the blank sheets corresponding to the respective layers of the sensor element 101 need to have the same thickness.

After the preparation of the blank sheets corresponding to the respective layers, pattern printing and dry are performed to form various patterns on the individual blank sheets (step S2). Specifically, electrode patterns of, for example, the sensing electrode 10 and the reference electrode 20, a pattern for forming the electrode protective layer 70 provided on the sensing electrode 10, and patterns for forming the heater 81 and the heater insulating layer 82, and patterns of forming an internal wire such as the heater lead (not illustrated) and the like are formed by printing. Additionally, in the first solid electrolyte layer 1, a cut mark is printed that serves as a reference cut position when the laminated body is cut in a subsequent step.

Each pattern is printed by applying a paste for pattern formation (such as conductive paste), prepared in accordance with the characteristic required for each formation target, to the blank sheet by a known screen printing technique. Any known drying means is available for dry after printing.

After the pattern printing, printing and drying of a bonding paste are performed to laminate and bond the green sheets corresponding to the respective layers (step S3). Any known screen printing technique is available for printing of a bonding paste, and any known drying means is available for drying after printing.

Subsequently, crimping is performed in which the adhesive-applied green sheets are laminated in a predetermined order, and the laminated green sheets are crimped on the predetermined temperature and pressure conditions, to thereby form a laminated body (step S4). Specifically, green sheets that are lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body has been obtained as described above, subsequently, a plurality of parts of the laminated body are cut out as individual units (referred to as element bodies) of the sensor element 101 (step S5). The cut-out element bodies are fired under predetermined conditions (step S6). In other words, the sensor element 101 is produced by integrally firing the solid electrolyte layers and the electrodes. The firing temperature is preferably 1200° C. or higher and 1500° C. or lower (for example, 1365° C.). The integral firing performed in such a manner provides satisfactory adhesion strength to the respective electrodes of the sensor element 101.

The resultant sensor element 101 is housed in a predetermined housing and incorporated into a main body (not shown) of the gas sensor 100.

<Temperature Profile and Trapping of Poisoning Substance in Sensor Element>

The following describes trapping of a poisoning substance in the sensor element 101. Schematically, in the sensor element 101, the poisoning substance is trapped in the measurement gas introduction space 30 by devising a temperature profile inside the element.

FIG. 3 is a diagram illustrating a temperature profile in the sensor element 101. FIG. 3 illustrates the profile (temperature profile) of the temperature T of the sensor element 101 in an X-axis direction, where the position of the open end 30e of the measurement gas introduction space 30 at the distal end E1 is taken to be an origin, and the direction (element longitudinal direction) in which the sensor element 101 extends from the position of the origin is taken to be the X axis. The position of the sensing electrode 10 is taken to be X=X0. The position of the sensing electrode 10 is represented by the position of the barycenter of the sensing electrode 10.

In the sensor element 101, as described above, the sensing cell including the sensing electrode 10 is heated to the temperature T0 of 400° C. or higher and 600° C. or lower, preferably 450° C. or higher and 550° C. or lower, by the heater 81. In other words, the sensor element 101 is heated so that the temperature T is T0 at X=X0.

In addition, as illustrated in FIG. 3, the sensor element 101 is heated by the heater 81 so that a place (X=Xmax) at which the temperature T is at a highest temperature Tmax exists in the range of 0≤X≤X0, that is, on a side of the sensing electrode 10 closer to the distal end E1, and the temperature T monotonically decreases from X=Xmax to X=X0. The temperature T=Tmax is any temperature equal to or higher than a melting point (or an estimated value of the melting point or the upper limit of an estimated range thereof) T1 (>T0) of the poisoning substance. The melting point T1 may be determined or estimated by an appropriate method. The highest temperature Tmax may be T1.

In FIG. 3, the relation T≥T1 holds in a range ΔX1 from X=X1 toward the distal end E1, and the place at which T=Tmax exists in the range. The relation T<T0 holds on a side of the sensing electrode 10 closer to the base end E2.

Since the temperature T=T1 is at least equal to or higher than the melting point of the poisoning substance, the poisoning substance exists in liquid or gas in the range in which the relation T≥T1 holds. Thus, when the sensor element 101 is provided with a temperature profile as described above through the heating by the heater 81, any poisoning substance having entered into the measurement gas introduction space 30 is once heated to the temperature T≥T1 in a first region of X≤X1 to become liquid or gas, and then gradually cooled in a second region of X≥X1 in which T<T1 holds, and all condenses before reaching at X=X0. Accordingly, the poisoning substance adheres to the fourth solid electrolyte layer 4, the fifth solid electrolyte layer 5, and the sixth solid electrolyte layer 6 partitioning the measurement gas introduction space 30 (serving as wall surfaces of the measurement gas introduction space 30) in the range of X1≤X≤X0. FIG. 3 exemplarily illustrates that an adhesion region RE is formed in a predetermined range from X=X1 toward the base end E2 through the adhesion of the poisoning substance.

This indicates that, as long as the distance of X1–X0 is sufficient, any poisoning substance having entered into the measurement gas introduction space 30 does not reach at the sensing electrode 10 nor the electrode protective layer 70 but is trapped halfway through. In such a case, no degradation of measurement accuracy due to adhesion of the poisoning substance to the sensing electrode 10 occurs even though the gas sensor 100 is continuously used for a long time.

In reality, a position at which T=T1 is not necessarily clearly specified, and thus it is favorable that the distance of Xmax–X0 between the position X=Xmax at which T=Tmax and the position X=X0 of the sensing electrode 10 is sufficiently secured, so as to trap the poisoning substance halfway through the measurement gas introduction space 30.

However, the value of the distance of X1–X0 or Xmax–X0 for enabling such trapping of the poisoning substance differs between temperature profiles, and thus is not necessarily unambiguously specified but may be experimentally or empirically specified.

As described above, according to the present preferred embodiment, a sensor element of a mixed-potential type gas sensor includes a measurement gas introduction space opening at a distal end and extending in the element longitudinal direction, and a sensing electrode provided on a most inner side of the measurement gas introduction space. When the gas sensor determines the concentration of a measurement target gas component, heating is performed by a heater provided to the sensor element to obtain such a temperature profile that a high temperature place, having a temperature higher than that at the sensing electrode and the melting point of a poisoning substance, exists between the open end and the sensing electrode and the temperature monotonically decreases between the high temperature place and the sensing electrode in a direction toward the sensing electrode from the open end. With this configuration, any poisoning substance having entered into the measurement gas introduction space through the open end is trapped before reaching at the position of the sensing electrode, which desirably prevents poisoning of the sensing electrode. Accordingly, no degradation of the sensitivity characteristic due to the poisoning substance occurs when the gas sensor is continuously used.

[Example]

(Experimental Example: Estimation of Melting Point of Poisoning Substance)

Figure 4:
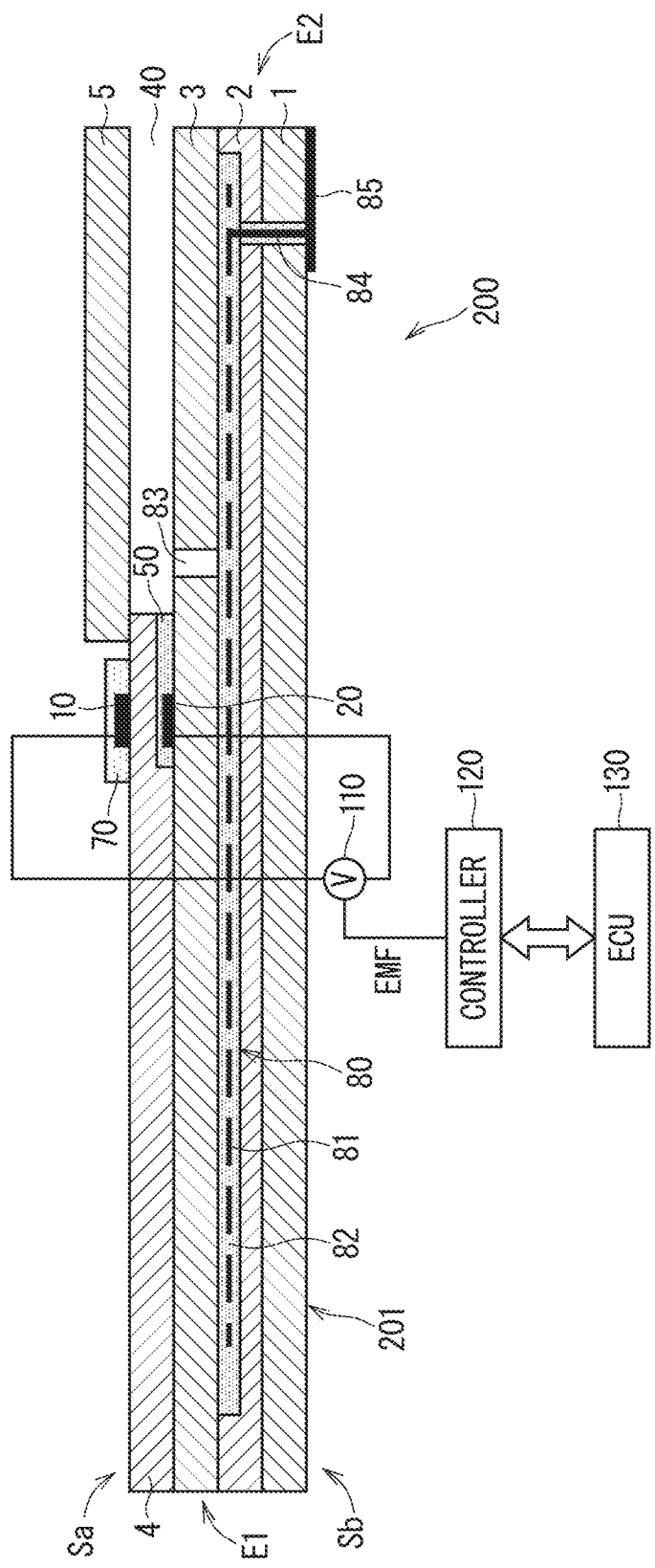
FIG. 4 is a diagram illustrating a gas sensor 200 used to estimate the melting point of a poisoning substance.

The following exemplarily describes estimation of the melting point T1 of the poisoning substance. FIG. 4 is a diagram illustrating a gas sensor 200 used for the estimation.

The gas sensor 200 has a configuration same as that of the gas sensor 100 except that a sensor element 201 does not include the sixth solid electrolyte layer 6, which is included in the sensor element 101, and thus includes no measurement gas introduction space 30, so that the electrode protective layer 70 is directly exposed outside the sensor element 201. Thus, each component of the gas sensor 200 is denoted by a reference sign identical to that of the corresponding component of the gas sensor 100, and description thereof will be omitted.

The following describes a case in which P (phosphorus) is assumed as a primary component of a poisoning substance, a phosphorus poisoning test is performed on the gas sensor 200 having a configuration as described above, and the melting point of the poisoning substance is estimated based on a result of the test. Since the sensor element 201 does not include the sixth solid electrolyte layer 6 unlike the sensor element 101, it is expected that the poisoning substance almost certainly adheres to at least the electrode protective layer 70 when the poisoning test is performed.

The phosphorus poisoning test was performed by installing the gas sensor 200 at an exhaust pipe of a gasoline engine (displacement: 1.8 L), and driving, for 70 hours, the engine using fuel obtained by mixing 0.25 mL of an engine oil additive (lubricant additive) as the poisoning substance into 1 L of gasoline.

Figure 5A:
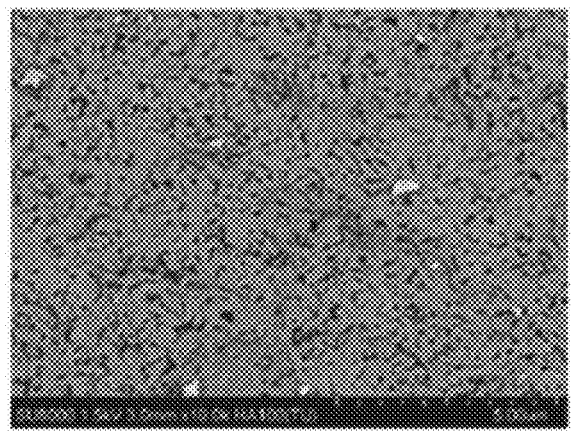
FIGS. 5A and 5B are each a surface SEM image of an electrode protective layer 70 before and after a poisoning test.
Figure 5B:
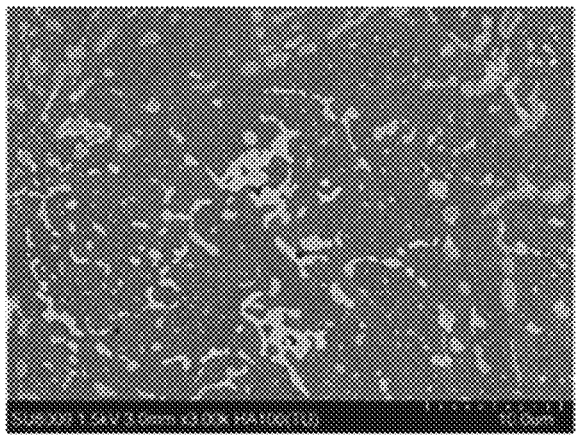

FIGS. 5A and 5B illustrate surface SEM images of the electrode protective layer 70 before and after the poisoning test. In the SEM image before the test in FIG. 5A, it is confirmed that a large number of fine pores, which appear in black, are distributed. On the other hand, in the SEM image after the test in FIG. 5B, none of such pores are found, but the state that the poisoning substance in gray and white is uniformly present is confirmed. By contrast with them, it is judged that clogging due to the poisoning substance occurs in the electrode protective layer 70 after the test.

In FIG. 5B, the poisoning substance is distributed flat (flattened without undulation) throughout, and thus it is presumed that the poisoning substance is in a glass state.

In addition, an XPS analysis was performed on the surface of the electrode protective layer 70 after the poisoning test. The XPS analysis was performed under analysis conditions listed below.

Device name: AXIS-HS manufactured by SHIMADZU/KRATOS;
X-ray source: Monochrome Al;
Tube voltage, tube current: 15 kV, 15 mA;
Lens condition: HYBRID (analysis region: 600 μm×1000 μm);
Measurement was performed under irradiation with electron ray.

Table 1 lists main detected elements in the XPS analysis and the abundance ratios (atm %) thereof.

TABLE 1

| Zr | O | C | Na | P | Zn | Al |
|---|---|---|---|---|---|---|
| 0.7 | 58.9 | 9.3 | 2 | 14 | 4.7 | 10.4 | atom %

Among the detected elements listed in Table 1, Al (aluminum) is an element attributable to the electrode protective layer 70, and Zr (zirconium) is a material attributable to the sensing electrode 10. Thus, it is determined from at least the result of the XPS analysis that the poisoning substance contains P (phosphorus), Zn (zinc), and Na (sodium) in amounts larger in this order. In addition, taking into consideration the SEM image illustrated in FIG. 5B, it is determined that any poisoning substance adhering to the electrode protective layer 70 is mainly glass oxide containing Zn in a P-rich phase and slightly containing Na.

Then, the melting point of the poisoning substance adhering to the electrode protective layer 70 was estimated in view of a known $ZnO$—$P_2O_5$ phase diagram (Katnack, F. L. et al., J. Electrochem. Soc. 1958, vol. 105, no. 3, p. 125, FIG. 4) illustrated in FIG. 6. To simplify the estimation, Na was excluded from consideration because of its small contained amount.

According to a result of detection through the XPS analysis listed in Table 1, the ratio of the numbers of P and Zn atoms in the poisoning substance is P:Zn=14:4.7. Based on the above atom number ratio, when it is assumed that P and Zn, in the poisoning substance expected to be in a glass state in reality exist as stable oxide $P_2O_5$ and $ZnO$, respectively, which are illustrated in the phase diagram in FIG. 6, the mole ratio of them is calculated to be $P_2O_5$:$ZnO$=7:4.7.

Figure 6:
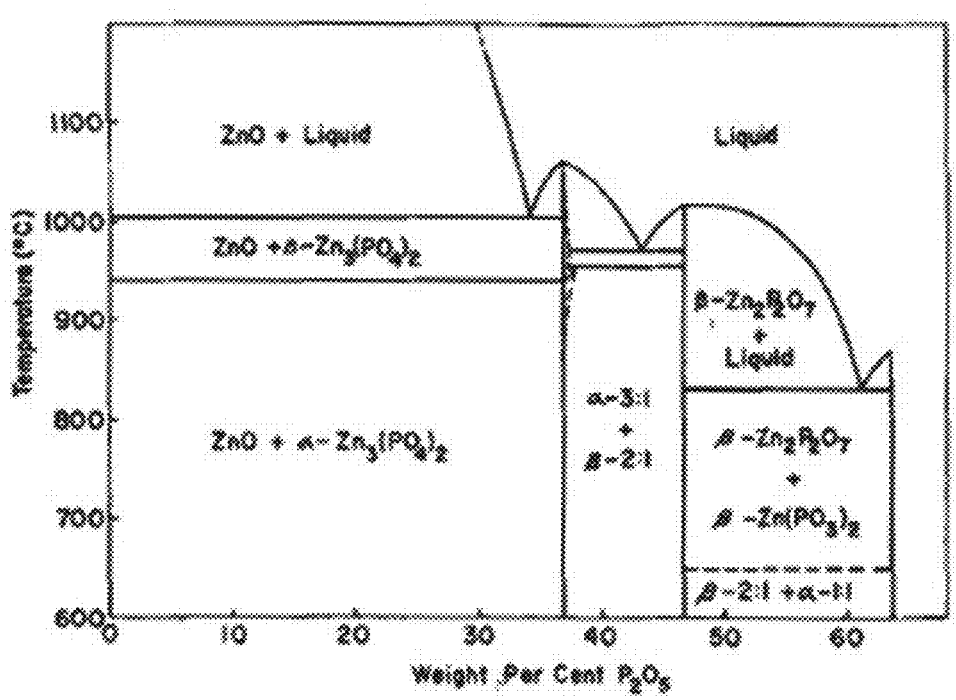
FIG. 6 is a ZnO—$P_2O_5$ phase diagram.

In order to apply to the phase diagram in FIG. 6, this mole ratio is converted to a mass ratio of $P_2O_5$ to the total mass of $P_2O_5$ and $ZnO$, which is $$P_2O_5/(P_2O_5+ZnO) \approx 70\ wt\ \%$$

since the molecular weight of $P_2O_5$ is 141.94 and the molecular weight of $ZnO$ is 81.41.

In the phase diagram in FIG. 6, $P_2O_5$ at 70 wt % is in a liquid phase in a range of 600° C. at least or higher. Thus, since the poisoning substance is in a glass state in reality and the melting point of single-phase $P_2O_5$ crystal is 360° C., the melting point T1 of the poisoning substance adhering to the electrode protective layer 70 through the poisoning test is estimated to be equal to or higher than 360° C. and equal to or lower than 600° C.

Thus, when the it is assumed that the poisoning substance mainly contains P at the use of the gas sensor 100, the poisoning substance can be trapped halfway through the measurement gas introduction space 30 by setting the temperatures T0 and Tmax that satisfy at least Tmax≥600° C.>T0 (≥400° C.).

(Example and Comparative Example)

As an example, the sensitivity characteristic (dependency of the sensor output EMF on the concentration of the measurement target gas component) of the gas sensor 100 according to the above-described preferred embodiment was evaluated before and after a phosphorus poisoning test. In addition, as a comparative example, the sensitivity characteristic of the gas sensor 200 used in the experimental example was evaluated before and after a phosphorus poisoning test. Each phosphorus poisoning test was performed under a condition same as that of the experimental example described above. In the gas sensor 100 and the gas sensor 200, X0 was 8.5 mm.

The evaluation of the sensitivity characteristic was performed by using model gasses. Specifically, with the gas sensor 100 or 200 being placed in a model gas whose concentration of a measurement target gas component is known, sensor output was acquired for different concentrations of the measurement target gas component in the model gas.

Two kinds of model gasses were prepared: model gas A containing $C_2H_4$ as a measurement target gas component, and model gas B containing CO as a measurement target gas component. The component of each model gas was as follows.

[Model Gas A]
$C_2H_4$: 0 ppm, 50 ppm, 70 ppm, 100 ppm, 200 ppm, 300 ppm, 500 ppm, 700 ppm, or 1000 ppm;
$O_2$: 10%;
$H_2O$: 5%;
$N_2$: balance

[Model Gas B]
CO: 0 ppm, 100 ppm, 300 ppm, 500 ppm, 700 ppm, 1000 ppm, or 2000 ppm;
$O_2$: 10%;
$H_2O$: 5%;
$N_2$: balance In the example and the comparative example, the evaluation of the sensitivity characteristic was performed twice for two temperature profiles with different combinations of the temperatures T0 and Tmax. The combinations of the temperatures T0 and Tmax in the temperature profiles are as follows.

Temperature Profile 1: T0=450° C., Tmax=600° C.;
Temperature Profile 2: T0=500° C., Tmax=650° C.

These temperature profiles were determined based on the estimation of T1≤600° C. from the result of the experimental example described above. In both temperature profiles, Xmax was defined as 3.0 mm.

Figure 7A:
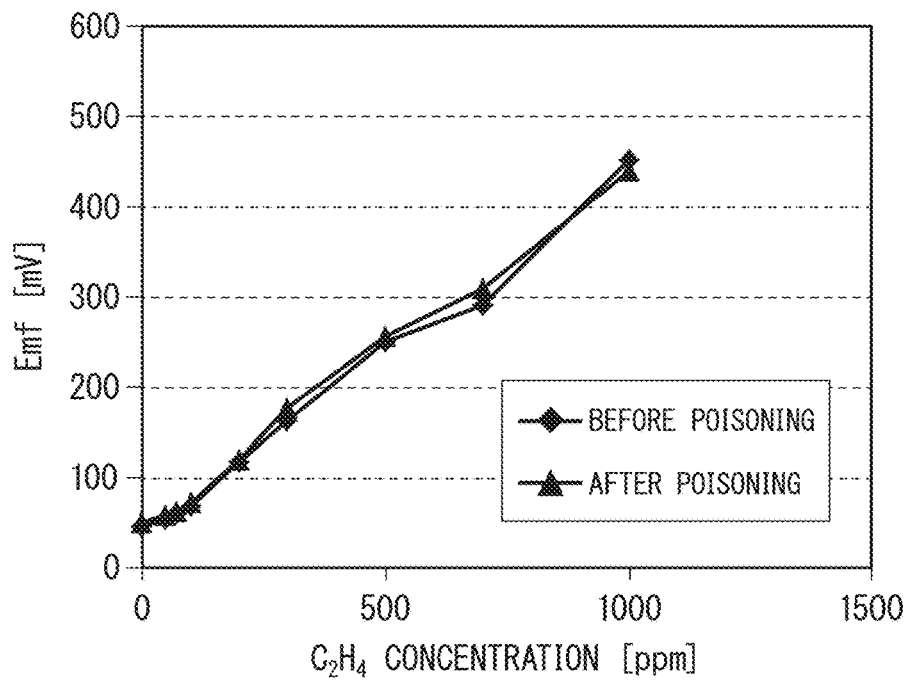
FIGS. 7A and 7B are each a diagram illustrating a result of evaluation of a sensitivity characteristic of the gas sensor 100 according to an example when Temperature Profile 1 is applied.
Figure 7B:
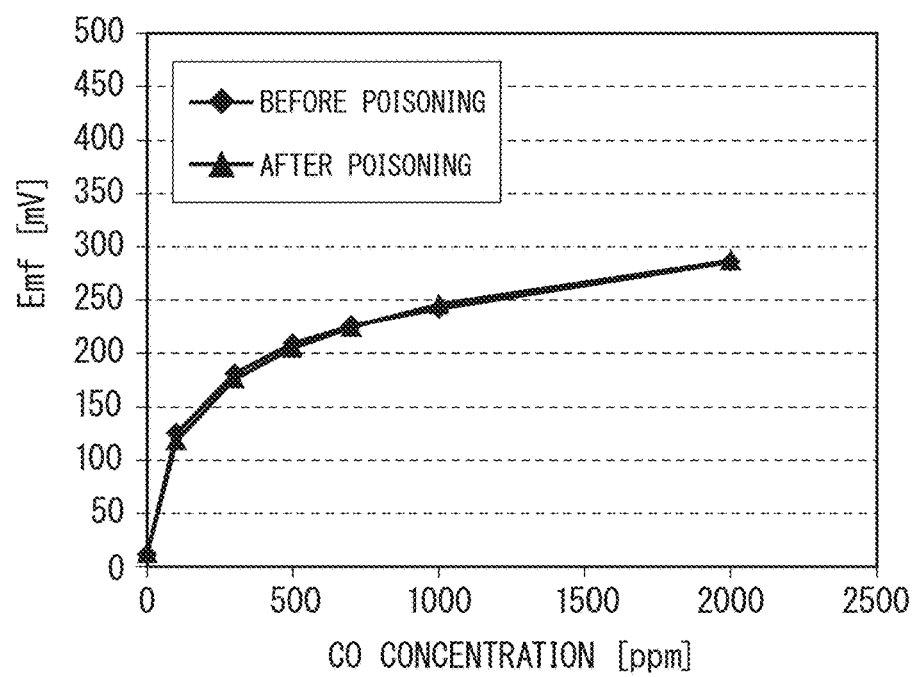
Figure 8A:
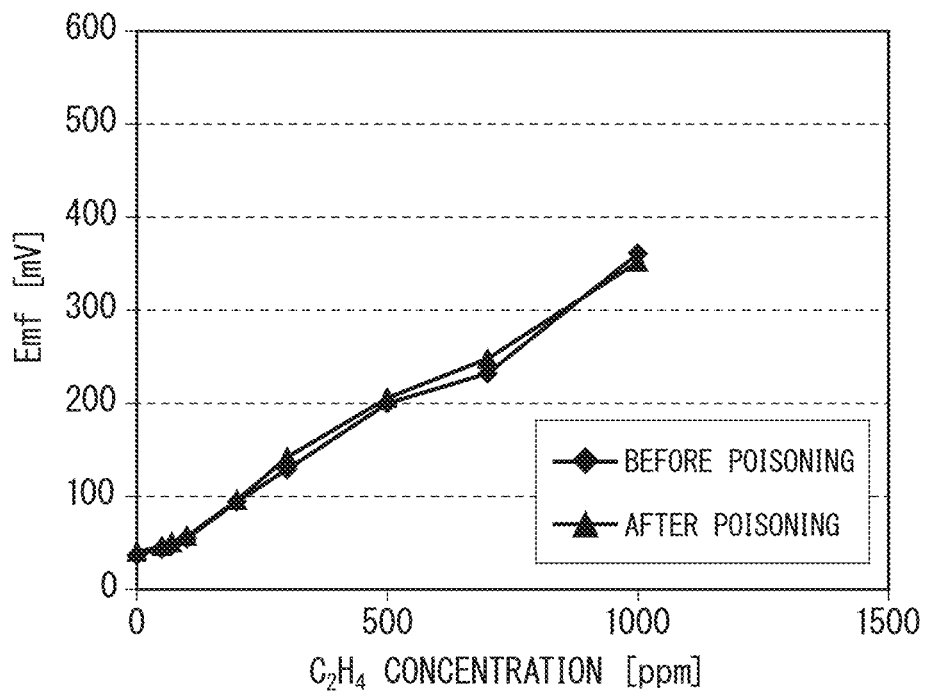
FIGS. 8A and 8B are each a diagram illustrating a result of evaluation of the sensitivity characteristic of the gas sensor 100 according to the example when Temperature Profile 2 is applied.
Figure 8B:
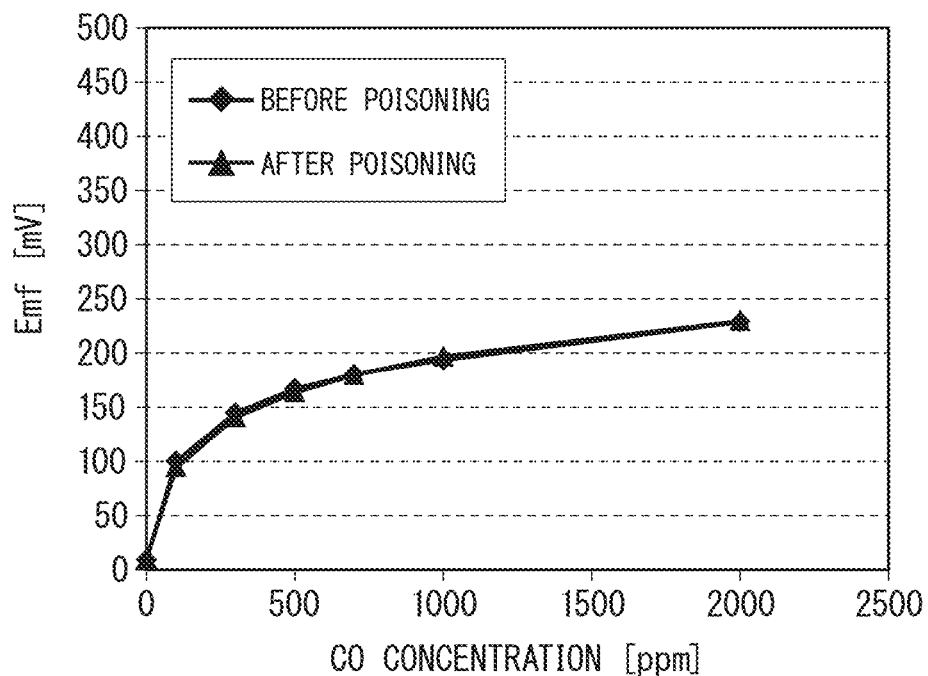
Figure 9A:
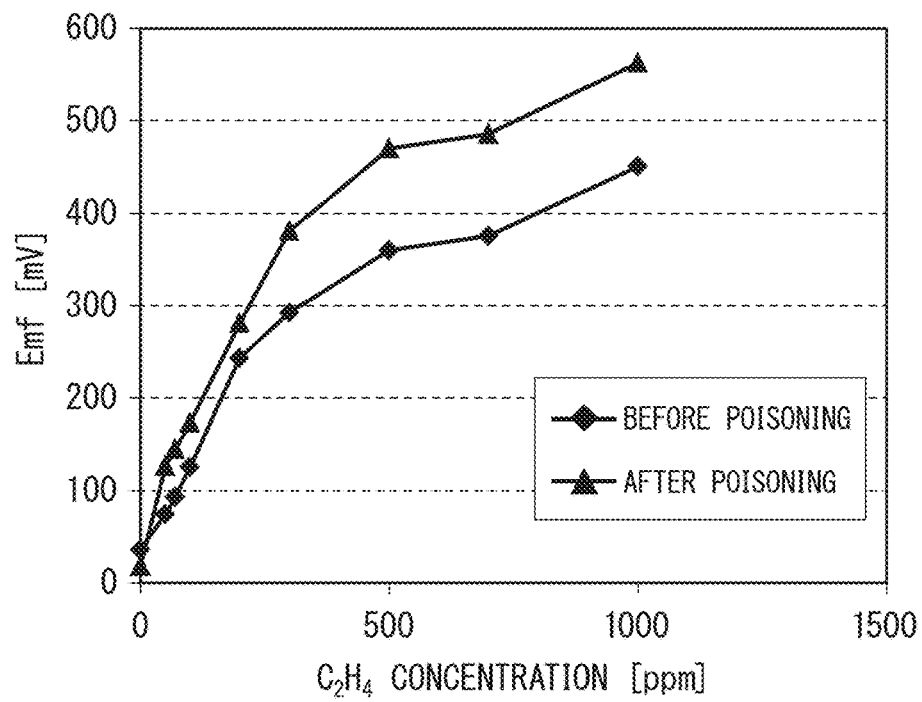
FIGS. 9A and 9B are each a diagram illustrating a result of evaluation of a sensitivity characteristic of the gas sensor 200 according to a comparative example when Temperature Profile 1 is applied.
Figure 9B:
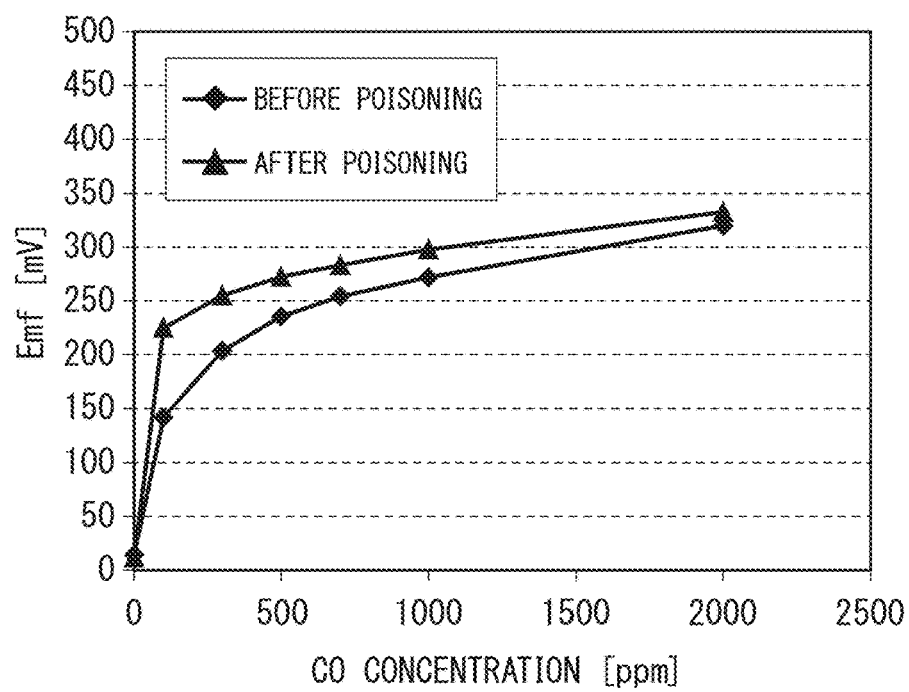
Figure 10A:
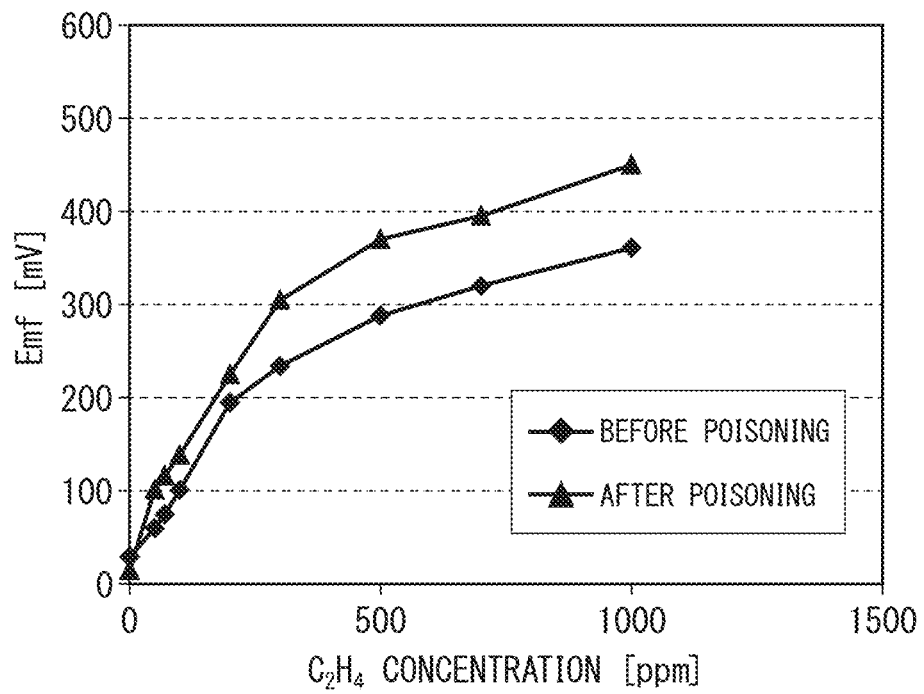
FIGS. 10A and 10B are each a diagram illustrating a result of evaluation of the sensitivity characteristic of the gas sensor 200 according to the comparative example when Temperature Profile 2 is applied.
Figure 10B:
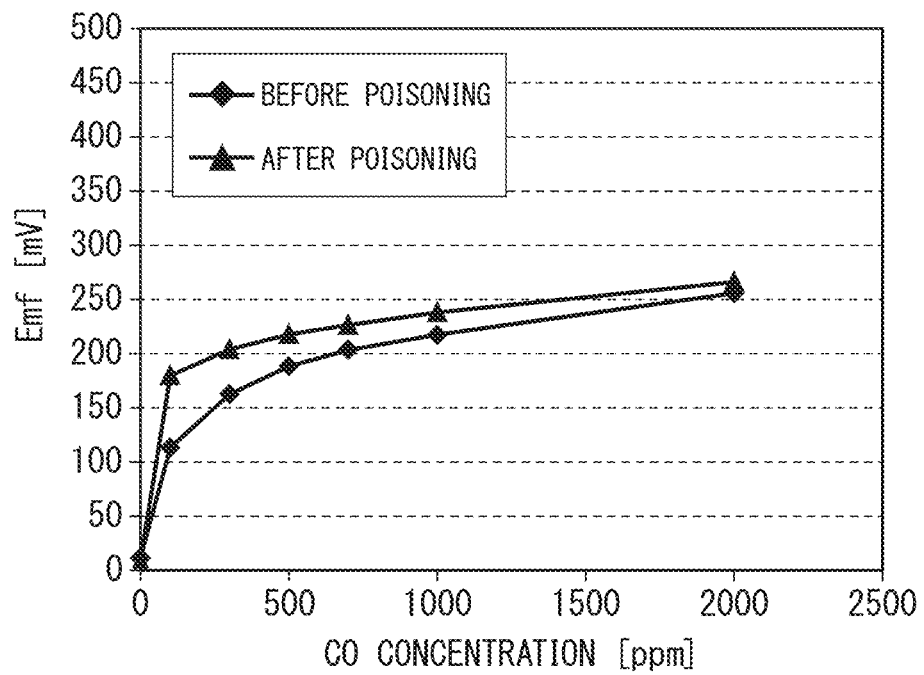

FIGS. 7A and 7B are each a diagram illustrating a result of evaluation of the sensitivity characteristic of the gas sensor 100 according to the example to which Temperature Profile 1 was applied, and FIGS. 8A and 8B are each a diagram illustrating a result of evaluation of the sensitivity characteristic of the gas sensor 100 to which Temperature Profile 2 was applied. FIGS. 9A and 9B are each a diagram illustrating a result of evaluation of the sensitivity characteristic of the gas sensor 200 according to the comparative example to which Temperature Profile 1 was applied, and FIGS. 10A and 10B are each a diagram illustrating a result of evaluation of the sensitivity characteristic of the gas sensor 200 to which Temperature Profile 2 was applied. FIGS. 7A, 8A, 9A, and 10A each illustrate an evaluation result for model gas A containing $C_2H_4$ as a measurement target gas component, and FIGS. 7B, 8B, 9B, and 10B each illustrate an evaluation result for model gas B containing CO as measurement target gas component.

As understood from FIGS. 9A, 9B, 10A, and 10B, the sensitivity characteristic of the gas sensor 200 according to the comparative example varied between before and after the poisoning test for any combination of a model gas and a temperature profile. However, as understood from FIGS. 7A, 7B, 8A, and 8B, the sensitivity characteristic of the gas sensor 100 according to the example hardly varied between before and after the poisoning test irrespective of the kind of a model gas and an applied temperature profile.

FIG. 11 illustrates an SEM image of the surface of the electrode protective layer 70 of the gas sensor 100 to which Temperature Profile 1 was applied and the sensitivity characteristic of which was evaluated by using model gas A after the poisoning test. This SEM image was acquired after the fifth solid electrolyte layer 5 and the sixth solid electrolyte layer 6 had been removed from the gas sensor 100 whose sensitivity characteristic evaluation had been finished, to expose an upper surface of the fourth solid electrolyte layer 4 and the electrode protective layer 70. The images of the poisoning substance found in the SEM image illustrated in FIG. 5B are not found in FIG. 11.

Figure 12:
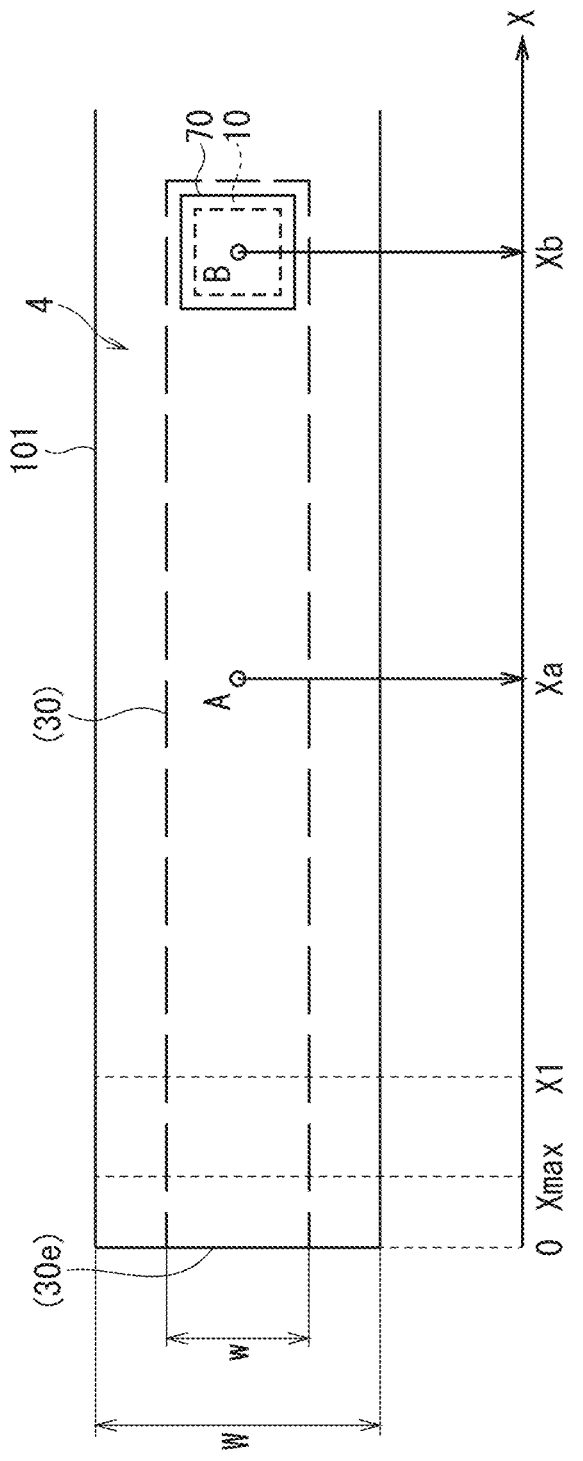
FIG. 12 is a diagram illustrating two analysis target positions listed in Table 2.

In addition, an XPS analysis was performed on the gas sensor 100, from which the SEM image illustrated in FIG. 11 was acquired, and where fifth solid electrolyte layer 5 and the sixth solid electrolyte layer 6 had been removed. Table 2 lists a result of the XPS analysis. FIG. 12 is a diagram illustrating two analysis target positions (points A and B) listed in Table 2. In FIG. 12, the sizes and ratios of components are different from those in reality for illustration and understanding. As illustrated in FIG. 12, points A and B are positions separated from the open end 30e (X=0) of the measurement gas introduction space 30 by distance Xa (=4.1 mm) and distance Xb (=7.7 mm), respectively, in the X-axis direction. Point A is a position in the measurement gas introduction space 30 (its original formation position is illustrated with a dashed line in FIG. 12) on a sufficiently inner side of X=Xmax at which the temperature T of the sensor element 101 is at the highest temperature Tmax. Point A is also a position estimated to be on a sufficiently inner side of X=X1. Point B is a position on the electrode protective layer 70 in the measurement gas introduction space 30 on a further inner side of point A. The sensor element 101 had a width W of 4.0 mm and a thickness of 1.2 mm, and the measurement gas introduction space 30 had an opening width w of 2.5 mm and a height (which is the thickness of the fifth solid electrolyte layer 5) of 0.2 mm. The shortest distance between the open end 30e and the electrode protective layer 70 (distance between the open end 30e and a left end part of the electrode protective layer 70 in FIG. 12) was 7.5 mm

TABLE 2

|  | Zr | Y | O | C | Na | Si | P | Zn | Al |
|---|---|---|---|---|---|---|---|---|---|
| Point A | 17.7 | 4.6 | 59.6 | 13.7 | 0.4 |  | 3 | 1 |  |
| Point B | 2.1 |  | 61.1 | 9 |  | 3.7 |  |  | 24.1 | atom %

Comparison between analysis results at points A and B indicates that P, Zn, and Na as components of the poisoning substance were detected at point A, but at point B, none of these elements were detected and only components included in the solid electrolyte layers and the electrode protective layer were detected. Si is impurity contained in the electrode protective layer. These results mean that any poisoning substance having entered into the measurement gas introduction space 30 at the poisoning test did not reach at the sensing electrode 10 and the electrode protective layer 70 disposed at the most inner part of the measurement gas introduction space 30.

The above-described result of the example indicates that, when such a temperature profile that temperature monotonically decreases toward the sensing electrode 10 between a place having a temperature higher than the melting point of the poisoning substance and the sensing electrode 10 is provided between the open end 30e of the measurement gas introduction space 30 and the sensing electrode 10 at operation of the gas sensor 100 according to the example, any poisoning substance having entered into the measurement gas introduction space 30 does not reach at the sensing electrode 10 and the electrode protective layer 70 disposed at the most inner part, and thus no adhesion of the poisoning substance that would affect the sensitivity characteristic occurs to the sensing electrode 10 and the electrode protective layer 70 when the gas sensor 100 is continuously used.

While the invention has been shown and described in detail, the foregoing description is in all aspects illustrative and not restrictive. It is therefore understood that numerous modifications and variations can be devised without departing from the scope of the invention.

What is claimed is:

1. A mixed-potential type gas sensor for sensing a predetermined gas component in a measurement gas, said sensor comprising a sensor element composed of an oxygen-ion conductive solid electrolyte, said sensor element including:
   a measurement gas introduction space having an open end at a distal end of said sensor element and extending in a longitudinal direction of said sensor element to an opposite end of said measurement gas introduction space which is opposite to said open end;
   a sensing electrode including a cermet of a noble metal and a first oxygen-ion conductive solid electrolyte and provided in said measurement gas introduction space at a position closer to said opposite end of said measurement gas introduction space than said open end;
   a reference electrode including a cermet of Pt and a second oxygen-ion conductive solid electrolyte; and
   a heater configured to heat said sensor element,
   wherein
   said gas sensor is configured to determine a concentration of said predetermined gas component based on a potential difference between said sensing electrode and said reference electrode, and
   when said gas sensor determines the concentration of said predetermined gas component, said heater heats said sensor element so that a high temperature region exists between said open end and said sensing electrode and a temperature decreases from said high temperature region toward said sensing electrode in the longitudinal direction of said sensor element toward said sensing electrode, said high temperature region having a temperature higher than a temperature of said sensing electrode and higher than a melting point of a predetermined poisoning substance.

2. The gas sensor according to claim 1, further comprising an electrode protective layer as a porous layer covering said sensing electrode.

3. A method of measuring a concentration of a predetermined gas component in a measurement gas through a mixed-potential type gas sensor including a sensor element composed of an oxygen-ion conductive solid electrolyte,
said sensor element including:
a measurement gas introduction space having an open end at a distal end of said sensor element and extending in a longitudinal direction of said sensor element to an opposite end of said measurement gas introduction space which is opposite to said open end;
a sensing electrode including a cermet of a noble metal and a first oxygen-ion conductive solid electrolyte and provided in said measurement gas introduction space at a position closer to said opposite end of said measurement gas introduction space than said open end;
a reference electrode including a cermet of Pt and a second oxygen-ion conductive solid electrolyte; and
a heater configured to heat said sensor element, and
said method comprising the steps of:
a) contacting the distal end of said sensor element with said measurement gas and contacting said reference electrode with a reference gas;
b) heating, in a contact state achieved through said step a), said sensor element by said heater, so that a high temperature region exists between said open end and said sensing electrode and a temperature decreases from said high temperature region toward said sensing electrode in the longitudinal direction of said sensor element toward said sensing electrode, said high temperature region having a temperature higher than a temperature of said sensing electrode and higher than a melting point of a predetermined poisoning substance; and
c) determining the concentration of said predetermined gas component based on a potential difference between said sensing electrode and said reference electrode while said sensor element is heated through said step b).

4. The gas sensor according to claim 1, wherein said predetermined poisoning substance is determined in advance to potentially exist in said measurement gas.

* * * * *